United States Patent

Balli et al.

[11] Patent Number: 4,506,073
[45] Date of Patent: Mar. 19, 1985

[54] CHROMENOAZAINDOLIZINE COMPOUNDS

[75] Inventors: Heinz Balli, Riehen; Sigmund Gunzenhauser, Arlesheim; Ian J. Fletcher, Magden; Davor Bedekovic, Therwil, all of Switzerland

[73] Assignee: Ciba-Geigy Corporation, Ardsley, N.Y.

[21] Appl. No.: 479,292

[22] Filed: Mar. 28, 1983

[30] Foreign Application Priority Data

Apr. 6, 1982 [CH] Switzerland .................. 2124/82

[51] Int. Cl.³ .................................. C07D 471/22
[52] U.S. Cl. .................................... 546/64; 546/121
[58] Field of Search ............... 546/62; 544/125, 78, 544/60, 361

[56] References Cited

FOREIGN PATENT DOCUMENTS 1951157 6/1971 Fed. Rep. of Germany ........ 546/62

Primary Examiner—Alan L. Rotman
Attorney, Agent, or Firm—Edward McC. Roberts; Kevin T. Mansfield

[57] ABSTRACT

The invention relates to chromenoazaindolizines of the general formula

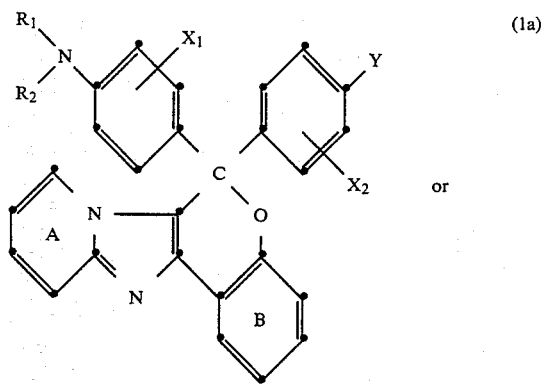

(1a)

or

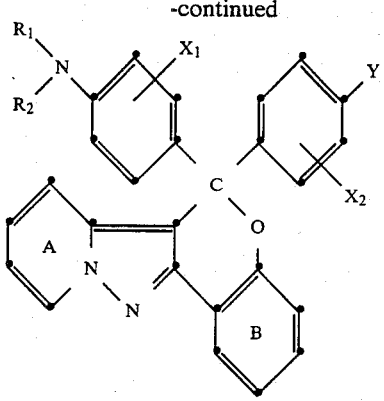

(1b)

wherein
each of Y, $X_1$ and $X_2$ independently of the other is hydrogen, halogen, lower alkyl, lower alkanoylamino or a group of the formula —$OR_3$    (1c)

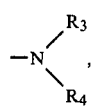

(1d)

each of $R_1$, $R_2$, $R_3$ and $R_4$ independently of the other is hydrogen, $C_1$-$C_{12}$ alkyl which is unsubstituted or substituted by halogen, hydroxy, cyano or lower alkoxy, or is cycloalkyl, phenyl, benzyl, or phenyl or benzyl each substituted by halogen, nitro, lower alkyl or lower alkoxy, or
each pair of substituents ($R_1$ and $R_2$) and ($R_3$ and $R_4$) independently of the other, together with the nitrogen atom to which said pair is attached, is a 5- or 6-membered heterocyclic radical; and
each of the rings A and B independently of the other is unsubstituted or substituted by halogen, nitro, lower alkyl, lower alkoxy, phenyl, phenoxy, or by an amino group which is unsubstituted or mono- or di-substituted by lower alkyl, phenyl, lower alkanoyl or benzyl.

These compounds are particularly suitable for use as color formers in pressure-sensitive or heat-sensitive recording materials and produce lightfast blue, greenish-blue or green colorations.

7 Claims, No Drawings

CHROMENOAZAINDOLIZINE COMPOUNDS

The present invention relates to chromenoazaindolizines, to the preparation thereof, and to the use thereof as colour formers in pressure-sensitive or heat-sensitive recording materials.

The chromenoazaindolizines of this invention have the general formula

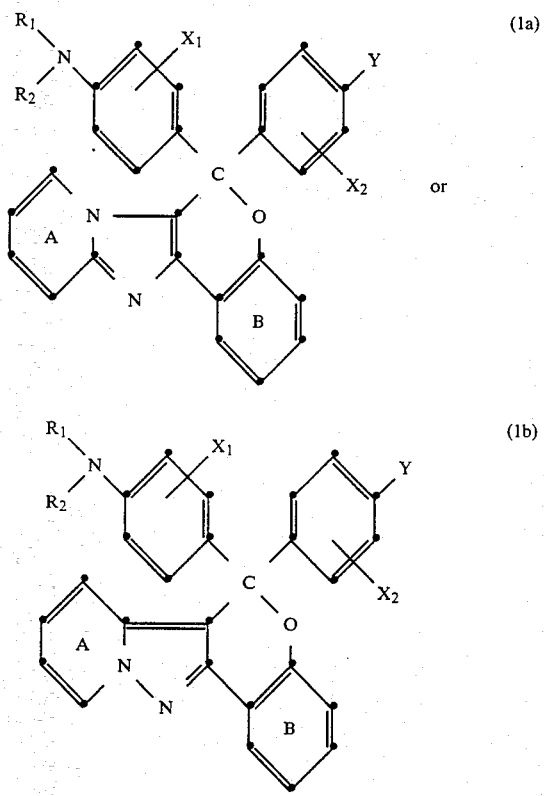

wherein
each of Y, X₁ and X₂ independently of the other is hydrogen, halogen, lower alkyl, lower alkanoylamino or a group of the formula —OR₃ or (1)

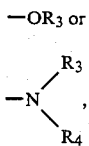

(1d)

each of R₁, R₂, R₃ and R₄ independently of the other is hydrogen, C₁–C₁₂ alkyl which is unsubstituted or substituted by halogen, hydroxy, cyano or lower alkoxy, or is cycloalkyl, phenyl, benzyl, or phenyl or benzyl each substituted by halogen, nitro, lower alkyl or lower alkoxy, or each pair of substituents (R₁ and R₂) and (R₃ and R₄) independently of the other, together with the nitrogen atom to which said pair is attached, is a 5- or 6-membered, preferably saturated, heterocyclic radical; and
each of the rings A and B independently of the other is unsubstituted or substituted by halogen, nitro, lower alkyl, lower alkoxy, phenyl, phenoxy, or by an amino group which is unsubstituted or mono- or disubstituted by lower alkyl, phenyl, lower alkanoyl or benzyl.

Y is preferably a group of the formula (1d). The groups of the formulae —NR₁R₂ and —NR₃R₄ may differ from each other or they are preferably identical. X₁ and X₂ are preferably also identical.

In the definition of the radicals of the chromenoazaindolizines, the term "lower" qualifying alkyl and alkoxy groups will normally be understood to denote groups which contain 1 to 5, preferably 1 to 3, carbon atoms. Examples of lower alkyl groups are methyl, ethyl, n-propyl, isopropyl, n-butyl, sec-butyl or amyl; and examples of lower alkoxy groups are methoxy, ethoxy or isopropoxy.

Lower alkanoylamino usually contains 2 to 5 carbon atoms and is e.g. acetylamino, propionylamino or butyrylamino. Halogen in connection with all substituents referred to above and hereinafter is preferably fluorine, bromine or, most preferably, chlorine.

R₁, R₂, R₃ and R₄ as alkyl groups may be straight chain or branched alkyl groups, e.g. methyl, ethyl, n-propyl, isopropyl, n-butyl, sec-butyl, amyl, n-hexyl, 2-ethylhexyl, n-octyl, isooctyl or n-dodecyl.

R₁, R₂, R₃ and R₄ as substituted alkyl groups are in particular cyanoalkyl, haloalkyl, hydroxyalkyl or alkoxyalkyl, each containing preferably a total of 2 to 4 carbon atoms, e.g. β-cyanoethyl, β-chloroethyl, β-hydroxyethyl, β-methoxyethyl or β-ethoxyethyl. R₁, R₂, R₃ and R₄ as cycloalkyl may be cyclopentyl or, preferably, cyclohexyl.

Preferred substituents in the benzyl moiety and in the phenyl moiety of the radicals R are e.g. halogens, nitro, methyl or methoxy.

Examples of such araliphatic and aromatic radicals are p-methylbenzyl, o- or p-chlorobenzyl, o- or p-nitrobenzyl, o- or p-tolyl, xylyl, o-, m- or p-chlorophenyl, o- or p-nitrophenyl, or o- or p-methoxyphenyl.

A heterocyclic radical represented by each pair of substituents (R₁ and R₂) and (R₃ and R₄), together with the nitrogen atom to which said pair is attached, is e.g. pyrrolidino, piperidino, picolino, morpholino, thiomorpholino or piperazino.

The substituents R₁, R₂, R₃ and R₄ are preferably benzyl, lower alkyl or cyano-lower alkyl, e.g. β-cyanoethyl.

X₁ and X₂ are preferably each hydrogen. However, they may also with advantage be methyl, methoxy, ethoxy, chlorine or acetylamino, each preferably in ortho-position to the carbon bond.

The nitrogen-containing ring A is preferably not further substituted.

The benzene ring B is preferably unsubstituted or substituted by 1 or 2 halogen atoms or by 1 or 2 lower alkyl or lower alkoxy groups, e.g. by chlorine, methyl, isopropyl, tert-butyl or methoxy. These substituents are preferably in the para-position or in the ortho- and para-position to the oxygen atom.

Useful chromenoazaindolizines are those of the formula

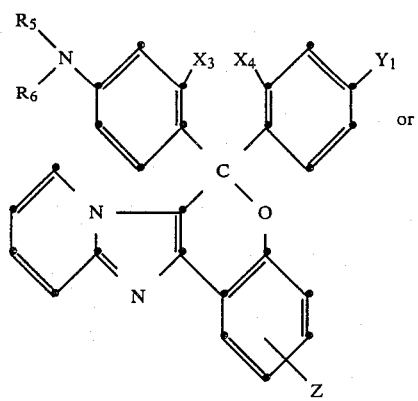 (2a)

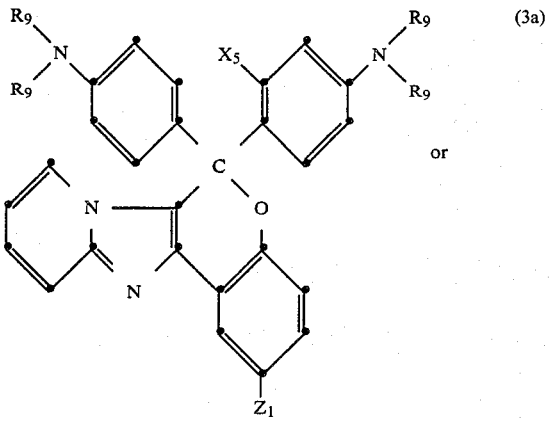 (3a)

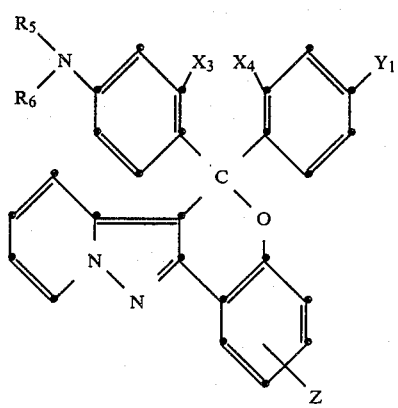 (2b)

(3b)

wherein

Y₁ is hydrogen, —OR₇ or

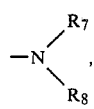

each of X₃ and X₄ independently of the other is hydrogen, halogen, methyl, methoxy, ethoxy or acetylamino, each of R₅, R₆, R₇ and R₈ independently of the other is lower alkyl, cyanoethyl, benzyl or phenyl, or each pair of substituents (R₅ and R₆) and (R₇ and R₈) independently of the other is pyrrolidino, piperidino or morpholino, and Z is hydrogen, halogen, lower alkyl, lower alkoxy, phenyl, or an amino group which is unsubstituted or mono- or disubstituted by lower alkyl, benzyl or phenyl groups.

Particularly preferred compounds of the formulae (2a) and (2b) are those in which Y₁ is the group of the formula —NR₇R₈, X₃ and X₄ are hydrogen and Z is hydrogen, halogen, methyl or methoxy.

Particularly interesting chromenoazaindolizines are those of the formula wherein R₉ is lower alkyl, preferably methyl or ethyl, X₅ is hydrogen, methoxy or ethoxy, and Z₁ is hydrogen, methyl, methoxy or halogen.

Particularly preferred compounds of the formulae (3a) and (3b) are those in which R₉ is methyl or ethyl, X₅ is hydrogen and Z₁ hydrogen, chlorine, methyl or methoxy.

The chromenoazaindolizines of the formula (1a) can be prepared by reacting a 1-azaindolizine of the formula

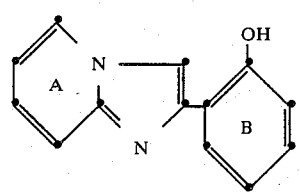 (4a)

or a 1-azaindolizinium compound of the formula

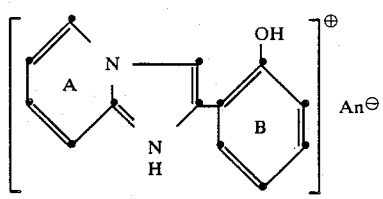 (4b)

with a carbinol of the formula

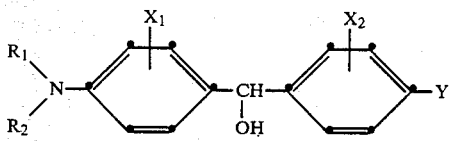

and subsequently oxidising the reaction product. In the above formulae, A, B, $R_1$, $R_2$, $X_1$, $X_2$ and Y have the given meanings and $AN^\ominus$ is the anion of an organic or preferably inorganic acid, e.g. the chloride, bromide, fluoride, sulfate, phosphate or, preferably, perchlorate ion.

The reaction is preferably carried out by first reacting the reactants in an organic solvent with is water-miscible and inert to the starting materials and then, after addition of an aqueous solution of an alkali metal carbonate or alkali metal hydroxide, oxidising the reaction product with an oxidising agent to give the chromeno compound.

When using the 1-azaindolizine of the formula (4a), the reaction is preferably carried out in the presence of an acid catalyst, e.g. a lower aliphatic carboxylic acid such as formic acid or acetic acid, or an inorganic acid such as hydrochloric acid, sulfuric acid, phosphoric acid or perchloric acid.

The reaction may be carried out in the temperature range from 10° to 100° C., preferably from 20° to 40° C. The oxidation step can be carried out in the temperature range from 0° to 100° C. It is convenient to carry out the oxidation in the range from room temperature (20° to 25° C.) to 100° C., preferably at room temperature.

Suitable organic solvents are preferably lower aliphatic alcohols, e.g. methanol, ethanol or isopropanol, or cyclic ethers, e.g. dioxane or tetrahydrofuran, γ-butyrolactone, acetonitrile, dimethylsulfoxide, dimethylformamide, dimethylacetamide or, in particular, N-methylpyrrolidone.

Examples of suitable alkali metal carbonates are potassium carbonate or sodium carbonate. Preferred alkali metal hydroxides are potassium hydroxide or sodium hydroxide.

Examples of suitable oxidising agents are chromates, bichromates, chlorates, chlorites, peroxides, manganese dioxide, lead dioxide, chlorine, bromine, molecular oxygen, air, perborates, permanganates, hydrogen peroxide, chloranil and, in particular, water-soluble salts of hexacyanoferrate(III). Preferred water-soluble salts of hexacyanoferrate(III) are the potassium and sodium salts. Instead of using commercially available tripotassium hexacyanoferrate(III), it is also possible to use solutions which are obtained by oxidation of potassium hexacyanoferrate(II) with hydrogen peroxide in the presence of an acid at room temperature.

The water-soluble salt of hexacyanoferrate(III) is employed in at least stoichiometric proportion. It is preferred to use 0.1 to 1.2 times the stoichiometric amount, i.e. 2.0 to 2.4 moles of hexacyanoferrate(III) per mole of each reactant.

When the oxidation is complete, the chromenoazaindolizine is isolated by removing the crude product from the reaction mixture by filtration and washing it with water until neutral. The resultant chromeno-1-azaindolizine is then purified over silica gel plates or by thin-layer chromatography and/or by recrystallisation.

The chromeno-3-azaindolizines of the formula (1b) are prepared by reacting a 3-azaindolizine of the formula

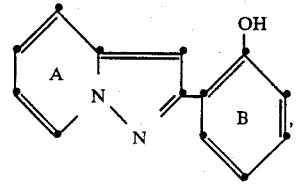

wherein A and B have the given meanings, with a carbinol of the formula (5) and subsequently oxidising the reaction product.

This reaction is also conveniently carried out in a polar organic solvent, preferably in a lower alkanol or in a cyclic ether such as dioxane or tetrahydrofuran, dimethylsulfoxide, acetonitrile, dimethylformamide, γ-butyrolactone or N-methylpyrrolidone, and preferably in the presence of an acid catalyst. The reaction may be carried out at room temperature (20° to 25° C.). Examples of suitable acid catalysts are lower aliphatic carboxylic acids such as formic acid or acetic acid, and inorganic acids such as hydrochloric acid, sulfuric acid, phosphoric acid or perchloric acid and also phosphoroxy chloride. If desired, the reaction product may be isolated.

The oxidation of the reaction product to give the chromeno-3-azaindolizine of the formula (1b) is carried out with an oxidising agent. Examples of suitable oxidising agents are chromates, bichromates, chlorates, chlorites, peroxides, manganese dioxide, lead dioxide, molecular oxygen, air, perborates, permanganates, hydrogen peroxide and chloranil.

The best results in respect of yield and purity of the chromeno-3-azaindolizines are obtained with a water-soluble salt of hexacyanoferrate(III), in particular with tripotassium hexacyanoferrate(III), which is employed preferably after addition of an aqueous solution of an alkali metal carbonate or, preferably, of an alkali metal hydroxide, e.g. potassium hydroxide, and conveniently in the presence of N-methylpyrrolidone.

The oxidation temperature depends usually on the oxidising agent and on the boiling point of the solvent employed, and is advantageously in the range from 20° to 100° C. When using potassium hexacyanoferrate(III), the oxidation is preferably carried out at room temperature.

The 1-azaindolizines of the formula (4a) can be obtained according to L. Schmid and K. Gründig, Monatshefte der Chemie, Vol 84, pp. 491–497. A preferred process for the preparation of the 1-azaindolizines of the formula (4a) comprises reacting a 2-haloacetylphenol of the formula

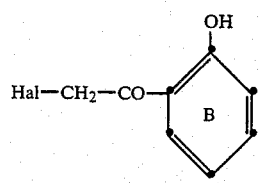

wherein B has the given meaning and halogen is e.g. bromine, iodine or chlorine, with a 2-aminopyridine of the formula

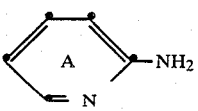

(8)

wherein A has the given meaning. The resultant 1-azaindolizine may be subsequently converted into the desired cycloammonium salt of the formula (4b) in a manner which is known per se.

Preferred starting materials of the formulae (4a) and (4b) are 2-(2-hydroxyphenyl)-1-azaindolizines or 2-(2-hydroxyphenyl)-1-azaindolizinium compounds in which the hydroxyphenyl radicals are unsubstituted or ring-substituted by methoxy, tert-butyl or, preferably, by chlorine or methyl.

The starting 3-azaindolizines of the formula (6) can be obtained by cyclising e.g. a 2-(alkoxyphenacyl)pyridine compound of the formula

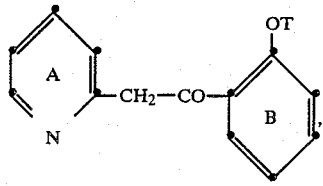

(9)

wherein T is $C_1$–$C_4$-alkyl, preferably methyl, with a solution of mesitylsulfonyl hydroxylamine in dichloromethane (prepared in accordance with Y. Tamura, J. Minamikawa, K. Sumoto, S. Fujii, M. Ikeda, J. Org. Chem., 38, 6, 1973, pp. 1239–41) to give the 2-(alkoxyphenyl)-3-azaindolizine of the formula

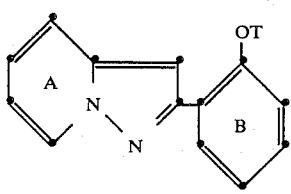

(10)

and dealkylating this compound with trimethylsilyliodide, in the temperature range from 30° to 120° C., to give the compound of the formula (6).

The 2-(alkoxyphenyl)-3-azaindolizines of the formula (10) can also be prepared by oxidising the corresponding Schiff's base of a 1-amino-2-picolinium salt in accordance with the particulars of German Offenlegungsschrift No. 2 118 917, or a 2-(β-amino-2'-alkoxyphenylethyl)pyridine in accordance with Bower, J. Chem. Soc. 1957, 4510, to give the 3-azaindolizine of the formula (10).

The preferred starting material of the formula (5) is 4,4'-bis-(dimethylamino)benzhydrol ("Michler's hydrol").

The chromenoazaindolizines of the formulae (1) to (3) are normally colourless or, at most, faintly coloured. When these colour formers are brought into contact preferably with an acid developer, e.g. an electron acceptor, they produce intense blue, greenish blue or green shades of excellent fastness to sublimation and light. They are therefore also very useful when mixed with one or more other known colour formers, for example 3,3-(bis-aminophenyl)-phthalides, 3,3-(bisindolyl)-phthalides, 3-aminofluoranes, 2,6-diaminofluoranes, leucoauramines, spiropyranes, spirodipyranes, chromenoindoles, phenoxazines, phenothiazines, carbazolylmethanes or other triarylmethane-leuco dyes, to give blue, navy blue, grey or black colorations.

The chromenoazaindolizines of the formulae (1) to (3) exhibit both on phenolic substrates and especially on activated clays an improved colour intensity and lightfastness. They are suitable in particular as rapidly developing colour formers for use in a heat-sensitive or especially in a pressure-sensitive recording material which can also be a copying material.

A pressure-sensitive material consists, for example, of at least one pair of sheets which contain at least one colour former of the formulae (1) to (3) dissolved in an organic solvent, and a solid electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, kaolin or any clay. Preferred developers are acidic organic compounds, for example unsubstituted or ring-substituted phenols, salicylic acid or salicylates and their metal salts, or an acidic polymer, for example a phenolic polymer, an alkylphenolacetylene resin, a maleic acid/rosin resin or a partially or completely hydrolysed polymer of maleic acid and styrene, ethylene or vinyl methyl ether, or carboxypolymethylene. Mixtures of these polymers can also be used. Particularly preferred developers are zinc salicylates or the condensation products of p-substituted phenols with formaldehyde. These latter may also contain zinc.

The developers may also be used with other basically inert or almost inert pigments. Examples of such pigments are: talcum, titanium dioxide, zinc oxide, chalk, clays such as kaolin, as well as organic pigments, e.g. urea/formaldehyde or melamine/formaldehyde condensates.

The colour former effects a coloured marking at those points where it comes into contact with the electron acceptor. In order to prevent the colour formers contained in the pressure-sensitive recording materials from becoming active prematurely, they are usually separated from the electron acceptor. This separation can conveniently be accomplished by incorporating the colour formers in foamlike, spongelike or honeycomblike structures. Preferably, the colour formers are enclosed in microcapsules, which as a rule can be ruptured by pressure.

When the capsules are ruptured by pressure, for example with a pencil, and the colour former solution is transferred in this manner to an adjacent sheet which is coated with an electron acceptor, a coloured area is produced. This colour results from the dye which is formed and which is absorbed in the visible range of the electromagnetic spectrum.

The colour formers are encapsulated preferably in the form of solutions in organic solvents. Examples of suitable solvents are preferably nonvolatile solvents, for example a polyhalogenated paraffin, such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethylphosphate, an aromatic ether such as benzylphenyl ether, a hydrocarbon oil such as paraffin or kerosene, an alkylated (e.g. with isopropyl, isobutyl, sec- or tert-butyl) derivative of diphenyl, naphthalene or triphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration and a viscosity which is advantageous for the microencapsulation.

The capsule walls can be formed evenly around the droplets of the colour former solution by coacervation; and the encapsulating material can consist of gelatin and gun arabic, as described e.g. in U.S. Pat. No. 2,800,457. The capsules can also be formed preferably from an aminoplast or a modified aminoplast by polycondensation, as described in British patent specification Nos. 989,264, 1,156,725, 1,301,052 and 1,355,124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (3) can be used for the production of a wide variety of known kinds of pressure-sensitive copying material. The various systems differ substantially from one another in the arrangement of the capsules, the colour reactants, i.e. the developers, and/or the support. A preferred arrangement is that in which the encapsulated colour former is in the form of a layer on the back of a transfer sheet and the developer is in the form of a layer on the face of a receiver sheet.

Another arrangement of the components is that wherein the microcapsules which contain the colour former, and the developer, are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinly alcohol, hydroxymethyl cellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of the formulae (1) to (3) can also be employed as colour formers in a thermoreactive recording material. This recording material usually contains at least one carrier, one colour former, one electron acceptor and, optionally, also a binder. Thermoreactive recording systems comprise, for example, heat-sensitive recording or copying materials or papers. These systems are used e.g. for recording information, for example in electronic computers, teleprinters or telewriters, or in recording and measuring instruments, e.g. electrocardiographs. The image (mark) formation can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer. Another possibility consists in dispersing both the colour former and the developer in one layer. By means of heat the binder is softened at specific areas and the colour former comes into contact with the developer (electron acceptor) at those points where heat is applied and the desired colour develops at once.

Suitable developers are the same electron acceptors as are used in pressure-sensitive papers. Examples of developers are the clays already mentioned and especially phenolic resins, or also the phenolic compounds described e.g. in German Offenlegungsschrift No. 1 251 348, for example 4-tert-butylphenol, 4-phenylphenol, 4-hydroxydiphenyl ether, α-naphthol, β-naphthol, 4-hydroxymethylbenzoate, 4-hydroxyacetophenone, 2,2'-dihydroxydiphenyl, 4,4-isopropylidenediphenol, 4,4'-isopropylidene-bis-(2-methylphenol), 4,4'-bis-(hydroxyphenyl) valeric acid, 2,2'-methylene-bis-(4-phenylphenol), hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the chromenoazaindolizines and the developer are reluctantly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers, for example polyvinyl alcohol, polyacrylic acid, hydroxyethylcellulose, methyl cellulose, carboxymethylcellulose, polyacrylamide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former and the developer are contained in one layer in a water-soluble binder.

The thermoreactive coatings may contain further ingredients. To improve the degree of whiteness, to facilitate the printing of papers, and to prevent the heated pen from sticking, the coatings may contain e.g. talcum, titanium dioxide, zinc oxide, aluminum hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, stearyl amide, phthalic anhydride, metal stearates, phthalonitrile or other appropriate fusible products which induce the simultaneous melting of the colour former and the developer. Thermographic recording materials preferably contain waves, e.g. carnauba wax, montan wax, paraffin wax or polyethylene wax.

The invention is illustrated by the following Examples, in which percentages are by weight, unless otherwise indicated.

EXAMPLE 1

6,6-bis(4-dimethylaminophenyl)-2-methyl-6H-chromeno[4,3-b]-1-azaindolizine 650 mg of 1H-2-(2-hydroxy-5-methylphenyl)-1-azaindolizinium perchlorate and 540 mg of 4,4'-bis(dimethylamino)benzhydrol are stirred in 15 ml of 1-methylpyrrolid-2-one for 3½ hours at room temperature and then 6 ml of aqueous 1N potassium hydroxide solution are added. Then 1.32 g of tripotassium hexacyanoferrate in 20 ml of water are added dropwise over 30 minutes. The crude product is precipitated by slowly stirring in 60 ml of water and the precipitate is isolated by filtration, purified over silica gel plates with a 3:1 mixture of toluene/ethyl acetate and subsequently recrystallised from methanol with the addition of a small amount of ammonia, copious water, and a small amount of potassium chloride. Yield:380 mg (40% of theory) of a compound of the formula

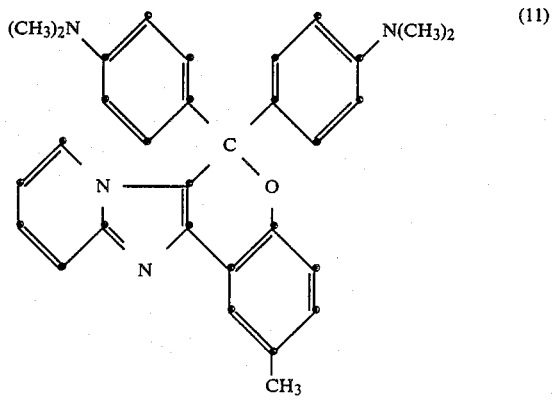

(11)

with a melting point of 241°–243° C. This colour former develops an intense blue colour on acid clay.

The 1-azaindolizinium perchlorate salt employed in this Example is obtained as follows:

10 mmoles of 2-bromacetyl-4-methylphenol and 10 mmoles of 2-aminopyridine are heated for 2–3 hours to 100° C. The crude product is triturated with a small amount of acetone to remove brown by-products, treated with ether and collected by filtration. The residue is taken up in ethanol and 70% perchloric acid is added to the ethanolic solution, followed by the addition of water until the onset of turbidity. The product precipitates in the form of pale beige-coloured needles. Yield:2.21 g (68% of theory). The resultant compound of the formula

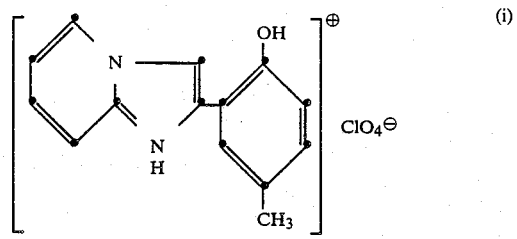

(i)

has a melting point of 231°–235° C.

EXAMPLE 2

6,6-bis(4-dimethylaminophenyl)-6H-chromeno-[4,3-b]-1-azaindolizine

The procedure described in Example 1 is repeated, replaciing the 1-azaindolizinium perchlorate of the formula (i) by 2.8 g of the bromide of the formula

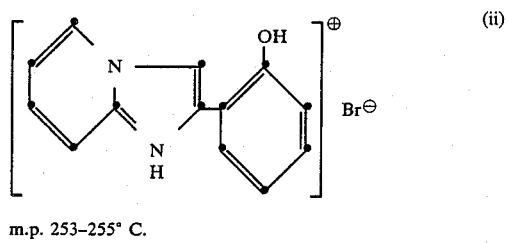

(ii)

m.p. 253–255° C.

to give 2.5 g of the compound of the formula

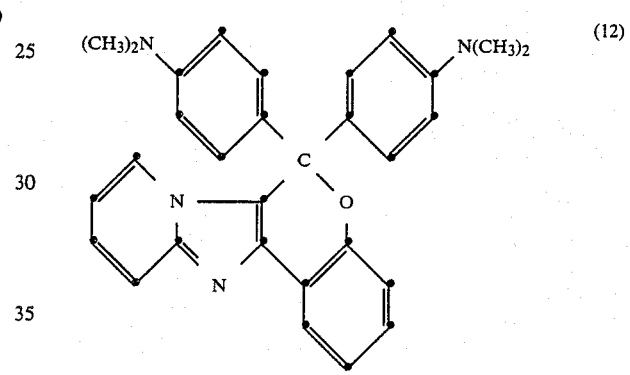

(12)

with a melting point of 268°–271° C. This colour former develops an intense blue colour on acid clay.

EXAMPLE 3

6,6-bis(4-dimethylaminophenyl)-2-methyl-6H-chromeno[3,4-a]-3-azaindolizine 450 mg of 2-(2-hydroxy-5-methylphenyl)-3-azaindolizine and 540 mg of 4,4'-bis(dimethylamino)benzhydrol are dissolved in 15 ml of 1-methylpyrrolid-2-one, then 280 mg of 70% perchloric acid are added and the mixture is stirred for 3 hours at room temperature. Then 6 ml of aqueous 1N potassium hydroxide solution are added and a solution of tripotassium hexacyanoferrate in 20 ml of water are added dropwise. The reaction mixture is subsequently diluted by the dropwise addition of 60 ml of water. The precipitate is isolated by filtration and taken up in toluene. The toluene solution is dried over anhydrous potassium carbonate and chromatographed over 100 g of silica gel by first eluting a few by-products with toluene. The main product is eluted with a 25:1 mixture of toluene/ethyl acetate and concentrated, affording as residue 390 mg (41% of theory) of pure colourless crystals (analysis by thin-layer chromatography). Recrystallisation from cyclohexane/hexane gives the compound of the formula

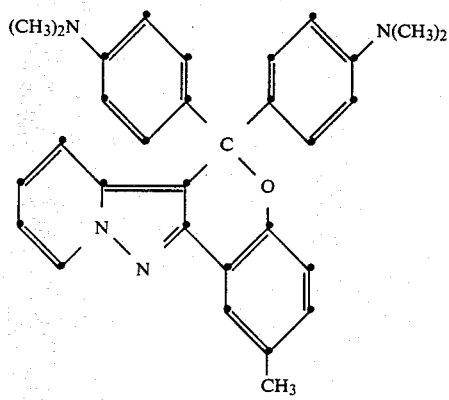

(13)

with a melting point of 230°–232° C. This colour former develops an intense blue colour on acid clay.

The 2-(2-hydroxy-5-methylphenyl)-3-azaindolizine used as starting material in this Example is obtained as follows:

With stirring, a solution of 15.6 g of α-picoline in 50 ml of absolute ether are added dropwise at −20° C. over 50 minutes to 100 ml of a 15% solution of n-butyllithium in hexane and 35 ml of absolute ether. The reaction mixture is then heated for 30 minutes at reflux, the heating bath is removed, and 14.9 g of methyl-2-methoxy-5-methylbenzoate in 40 ml of absolute ether are added dropwise such that gentle reflux is maintained. When the addition of benzoate is complete, the reaction mixture is heated for 30 minutes, diluted with 40 ml of water and poured into 100 g of a 1:1 mixture of ice/concentrated 6N hydrochloric acid. The mixture is extracted repeatedly with a total of 450 ml of 6N hydrochloric acid and the combined extracts are partially neutralised with 30% aqueous sodium hydroxide solution and adjusted to pH 7 with sodium bicarbonate. The neutral solution is extracted with ether and the ethereal extracts are dried over anhydrous sodium sulfate and concentrated. The residue is distilled in a high vacuum at 143°–147° C./11–12 Pa. Yield: 13.1 g of 2-(2-methoxy-5-methylphenacyl)pyridine in the form of a yellow oil.

With stirring 4.0 g of the above pyridine compound in 30 ml of dichloromethane are added at 0°–3° C. to a solution of mesitylsulfonyl hydroxylamine in 30 ml of dichloromethane and the mixture is stirred for 1 hour at 0° C. and for 15 hours at room temperature. After removal of crystallised mesitylsulfonic acid, the rection product is chromatographed with a 6:2:1 mixture of toluene/dichloromethane/ethyl acetate. The eluate is concentrated, affording as residue 2.44 g (62% of theory) of 2-(2-methoxy-5-methylphenyl)-3-azaindolizine in the form of an oil which is distilled in a high vacuum at 155° C./9–10 Pa. 600 mg of pure 2-(2-methoxy-5-methylphenyl)-3-azaindolizine are stirred at 100° C. for 6–7 hours in 5 g of trimethysilyl iodide and the mixture is diluted with water. The mixture is then extracted repeatedly with toluene. The combined toluene extracts are shaken with aqueous sodium hydrogen sulfite solution, dried over anhydrous sodium sulfate and concentrated. The residue is chromatographed with toluene, affording 488 g (46% of theory) of pure 2-(2-hydroxy-5-methylphenyl)-3-azaindolizine of the formula

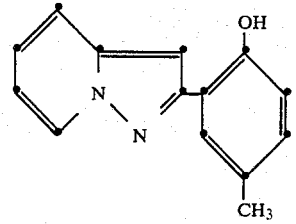

(iii)

which has a melting point of 108° C. after recrystallisation from petroleum ether.

EXAMPLE 4

Preparation of a pressure-sensitive copying paper

A solution of 3 g of the chromeno-3-azaindolizine of the formula (13) obtained in Example 3 in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with activated bentonite as colour developer. The first sheet and the sheet coated with the developer are laid on top of each other with the coated sides face to face. Pressure is exerted on the first sheet by writing by hand or typewriter and an intense blue copy of excellent lightfastness develops immediately on the sheet coated with the developer.

Correspondingly intense and lightfast blue copies are also obtained by using each of the other colour formers of the formulae (11) and (12) otained in Preparatory Examples 1 and 2 respectively.

EXAMPLE 5

1 g of the chromeno-1-azaindolizine of the fomula (11) is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by hand or typewriter and an intense and lightfast blue copy develops immediately on the sheet coated with the colour former.

EXAMPLE 6

Preparation of a heat-sensitive recording material

In a ball mill, 32 g of 4,4′-isopropylidenediphenol (bisphenol A), 3.8 g of the distearylamide of ethylenediamine, 39 g of kaolin, 20 g of an 88% hydrolysed polyvinyl alcohol and 500 ml of water are ground to a particle size of about 5 μm. In a second ball mill, 6 g of the chromeno-3-azaindolizine the formula (13) obtained in Example 3, 3 g of a 88% hydrolysed polyvinyl alcohol and 60 ml of water are ground to a particle size of about 3 μm.

Both dispersions are mixed and applied to paper to a dry coating weight of 5.5 g/m². An intense blue colour of excellent fastness to light and sublimation is produced by contacting the paper with a heated ball-point pen.

Intense and lightfast blue colorations are also obtained by, using each of the other colour formers of the formulae (11) and (12) obtained in Examples 1 and 2 respectively.

EXAMPLE 7

In a ball mill, 2.7 g of the chromeno-1-azaindolizine of the formula (11) obtained in Example 1, 24 g of N-phenyl-N'-(1-hydroxy-2,2,2trichloroethyl)urea, 16 g of stearylamide, 59 g of an 88% hydrolysed polyvinyl alcohol and 58 ml of water are ground to a particle size of 2–5 μm. This suspension is applied to a sheet of paper to a dry coating weight of 5.5 g/m². An intense and lightfast blue colour is obtained by contacting the paper with a heated ball-point pen.

What is claimed is:

1. A chromenoazaindolizine of the formula

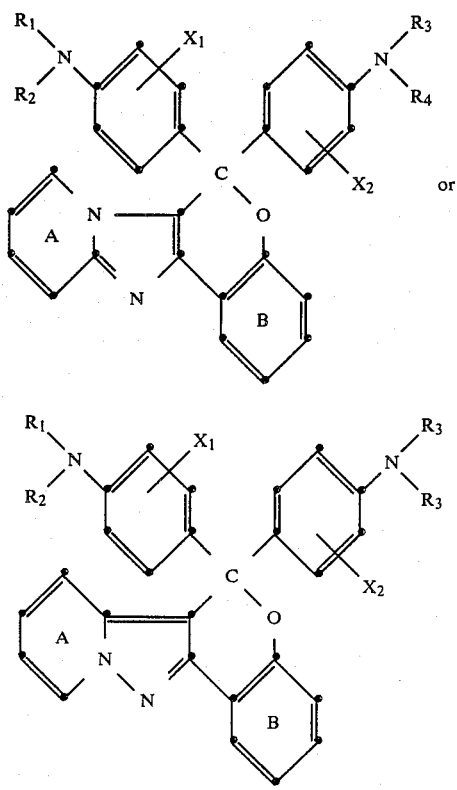

wherein each of $X_1$ and $X_2$ independently of the other is hydrogen, halogen, lower alkyl, lower alkanoylamino or a group of the formula

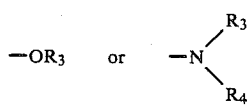

each of $R_1$, $R_2$, $R_3$ and $R_4$ independently of the other is hydrogen, $C_1$–$C_{12}$ alkyl which is unsubstituted or substituted by halogen, hydroxy, cyano or lower alkoxy, or is $C_5$–$C_6$ cycloalkyl, phenyl, benzyl, or phenyl or benzyl each substituted by halogen, nitro, lower alkyl or lower alkoxy, or each pair of substituents ($R_1$ and $R_2$) and ($R_3$ and $R_4$) independently of the other, together with the nitrogen atom to which said pair is attached, is a 5- or 6-membered heterocyclic radical; and each of the rings A and B independently of the other is unsubstituted or substituted by halogen, nitro, lower alkyl, lower alkoxy, phenyl, phenoxy, or by an amino group which is unsubstituted or mono- or disubstituted by lower alkyl, phenyl, lower alkanoyl or benzyl.

2. A chromenoazaindolizine of claim 1 of the formula

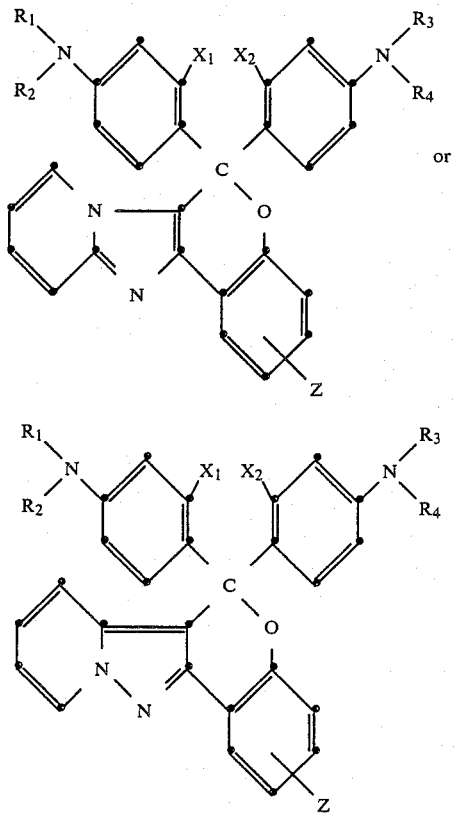

wherein each of $X_1$ and $X_2$ independently of the other is hydrogen, halogen, methyl, methoxy, ethoxy or acetylamino, each of $R_1$, $R_2$, $R_3$ and $R_4$ independently of the other is lower alkyl, cyanoethyl, benzyl or phenyl, or each pair of substituents ($R_1$ and $R_2$) and ($R_3$ and $R_4$) independently of the other is pyrrolidino, piperidino or morpholino, and Z is hydrogen, halogen, lower alkyl, lower alkoxy, phenyl, or an amino group which is unsubstituted or mono- or disubstituted by lower alkyl, benzyl or phenyl.

3. A chromenoazaindolizine of claim 2, wherein $X_1$ and $X_2$ are hydrogen and Z is hydrogen, halogen, methyl or methoxy.

4. A chromenoazaindolizine of claim 2 wherein $R_1$, $R_2$, $R_3$ and $R_4$ are all the same and are lower alkyl, $X_1$ is hydrogen, $X_2$ is hydrogen, methoxy or ethoxy, Z is hydrogen, methyl, methoxy or halogen and substituent Z is para to oxygen.

5. A chromenoazaindolizine of claim 4, wherein the R groups are all methyl or ethyl, $X_2$ is hydrogen, and Z is hydrogen, chlorine, methyl or methoxy.

6. A chromenoazaindolizine of claim 4, wherein in the first formula the R groups are all methyl, $X_2$ is hydrogen and Z is hydrogen or methyl.

7. A chromenoazaindolizine of claim 4, wherein in the second formula the R groups are methyl, $X_2$ is hydrogen and Z is methyl.

* * * * *

UNITED STATES PATENT AND TRADEMARK OFFICE
CERTIFICATE OF CORRECTION

PATENT NO. : 4,506,073

DATED : March 19, 1985

INVENTOR(S) : Heinz Balli, Sigmund Gunzenhauser, Ian J. Fletcher, and Davor Bedekovic.

It is certified that error appears in the above-identified patent and that said Letters Patent is hereby corrected as shown below:

Claim 1, column 15, line 37 should read--

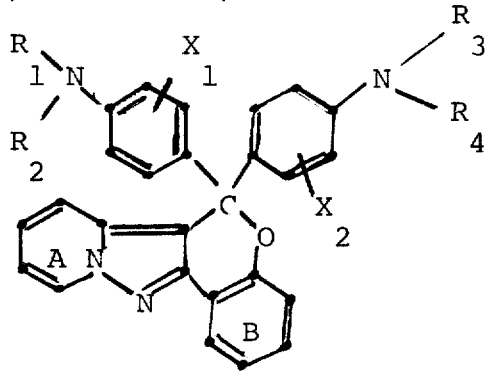

--.

Signed and Sealed this

Seventeenth Day of September 1985

[SEAL]

Attest:

Attesting Officer

DONALD J. QUIGG

Commissioner of Patents and Trademarks—Designate